US00PP33773P2

(12) United States Plant Patent
Grazzini

(10) Patent No.: US PP33,773 P2
(45) Date of Patent: Dec. 21, 2021

(54) *ARTEMISIA* PLANT NAMED 'G18123'

(50) Latin Name: ***Artemisia* hybrid**
Varietal Denomination: G18123

(71) Applicant: Garden Genetics, Bellefonte, PA (US)

(72) Inventor: Richard A. Grazzini, Bellefonte, PA (US)

(73) Assignee: Garden Genetics llc, Bellefonte, PA (US)

( * ) Notice: Subject to any disclaimer, the term of this patent is extended or adjusted under 35 U.S.C. 154(b) by 0 days.

(21) Appl. No.: 17/354,164

(22) Filed: Jun. 22, 2021

(51) Int. Cl.
*A01H 5/12* (2018.01)
*A01H 6/14* (2018.01)

(52) U.S. Cl.
USPC ..... Plt./373
CPC ..... *A01H 6/14* (2018.05)

(58) Field of Classification Search
USPC ..... Plt./373
CPC ..... A01H 6/14; A01H 5/12
See application file for complete search history.

*Primary Examiner* — Keith O. Robinson
(74) *Attorney, Agent, or Firm* — Cassandra Bright

(57) ABSTRACT

A new and distinct cultivar of *Artemisia* hybrid plant named 'G18123' is disclosed, characterized by compact, densely branched plants with mounded habits. The densely branching plants produce abundant vegetative terminal cuttings which have been shown to root easily. Foliage is small with shallow apical lobes and strong silver coloration. Plants frequently do not flower in the garden and have exceptional cold tolerance, observed to survive cold temperatures in USDA zone 5, both in the ground and in containers. The new variety is an *Artemisia*, and is normally used as a garden or container plant.

2 Drawing Sheets

Figure 1:
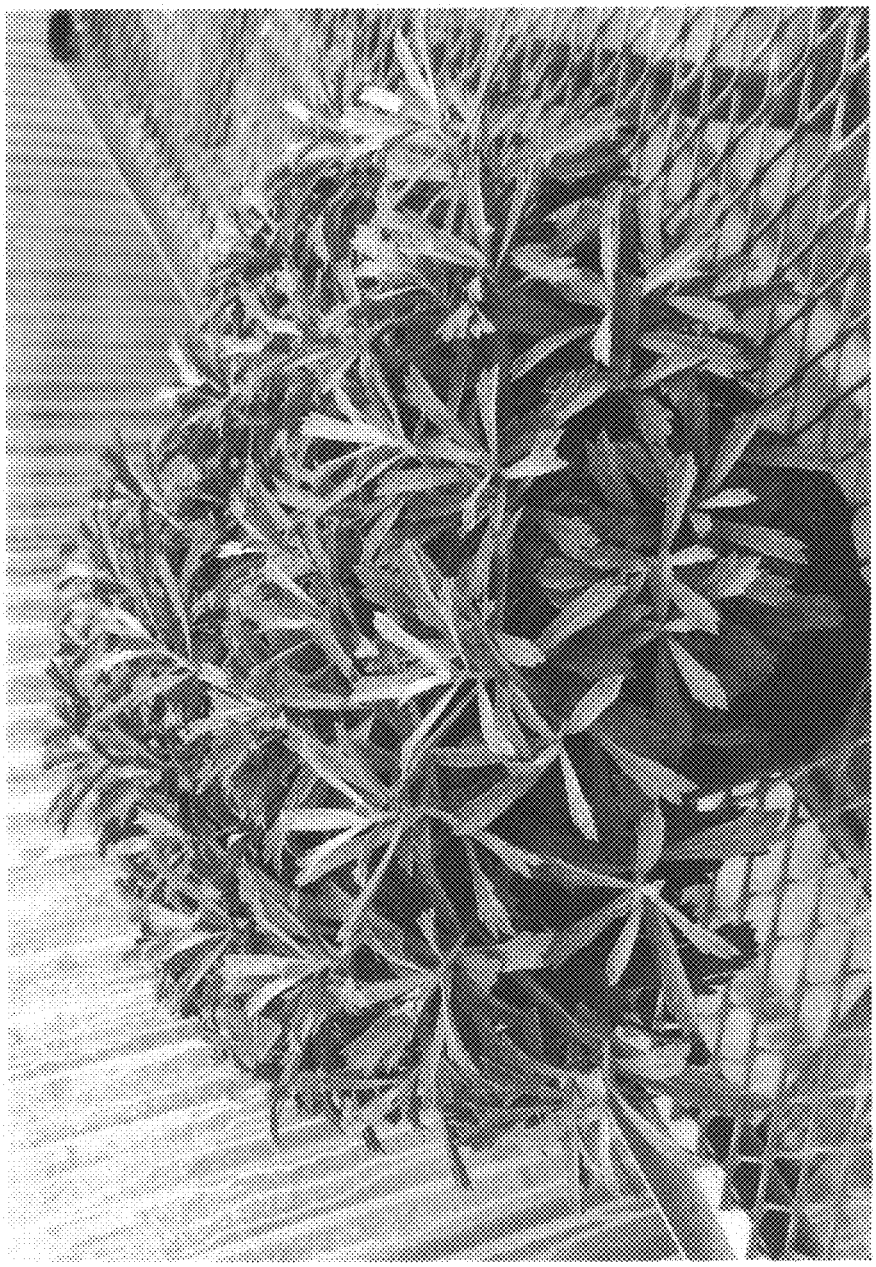

Latin name of the genus and species: *Artemisia* hybrid.
Variety denomination: 'G18123'.

BACKGROUND OF THE INVENTION

The new cultivar is the product of a planned hybridization by the inventor. The crossing resulting in the new variety was made in September of 2017 at a nursery in Bellefonte, Pa. The new variety was found and selected by the inventor in August of 2018 at the same nursery in Bellefonte, Pa.

Asexual reproduction of the new cultivar 'G18123' by terminal vegetative cuttings was performed at the same nursery in Bellefonte, Pa. in August 2016. Subsequently, asexual reproduction has shown that the unique features of this cultivar are stable and reproduced true to type through successive generations.

SUMMARY OF THE INVENTION

The cultivar 'G18123' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G18123.' These characteristics in combination distinguish 'G18123' as a new and distinct *Artemisia* cultivar:

1. Small leaves.
2. Brighter silver foliage color.
3. Compact garden habit.
4. Non-flowering in the garden, or if flowering will occur, very late flowering.

5. Exhibits a very high cutting yield per plant.
6. Unrooted cuttings are easy and quick to root.
7. Hardy perennial in at least USDA zone 5, in-ground and in-container.

PARENT COMPARISON

Plants of the new cultivar 'G18123' are similar to plants of the seed parent variety, the unpatented *Artemisia* '46900-1', in most horticultural characteristics. However, plants of the new cultivar 'G18123' differ in the following ways:

1. New variety 'G18123' has relatively small leaves, with only a few shallow lobes near the tip of the leaf. Leaves of seed parent '46900-1' are larger, and much more heavily lobed.;
2. New variety 'G18123' has intensely silvery-white foliage. Leaves of seed parent '46900-1' are much less silver, and much more green.
3. New variety 'G18123' has a compact, densely-branched, mounded habit, reaching a height and width of about 18-24" in the garden. Seed parent '46900-1' is much taller and broader, about 24-36" in height and width.;
4. New variety 'G18123' flowers very late in the season, and frequently fails to flower. Seed parent '46900-1' flowers profusely by mid- to late summer.
5. New variety 'G18123' is a hardy perennial, typically to USDA zone 4. Seed parent '46900-1' is much less hardy.

Plants of the new cultivar 'G18123' are similar to plants of the pollen parent variety, the unpatented *Artemisia* '46901-3', in most horticultural characteristics. However, plants of the new cultivar 'G18123' differ in the following ways:

1. New variety 'G18123' has relatively small leaves. Pollen parent '46901-3' has larger leaves both in length and width.

2. New variety 'G18123' is compact and densely-branched. Pollen parent '46901-3' is taller although also densely-branched.
3. New variety 'G18123' flowers very late in the season, and frequently fails to flower at all. Pollen parent '46901-3' flowers profusely in late summer.
4. New variety 'G18123' has intensely silvery-white leaves. Pollen parent '46901-3' has leaves which are less silver in appearance.

COMMERCIAL COMPARISON

'G18123' can be compared to the commercially known variety *Artemisia ludoviciana* 'Silver King', unpatented. These plants are similar in most horticultural characteristics. However, plants of the new cultivar 'G18123' differ in the following ways:

1. New variety 'G18123' has smaller leaves, typically 2.5-3.0" long by 0.5-0.75" wide. Comparison variety 'Silver King' has leaves which are typically both longer and wider than 'G18123'.
2. New variety 'G18123' has leaves which are consistently bright silvery-white. Leaves of comparison variety 'Silver King' are typically less silver in appearance.
3. New variety 'G18123' has leaves which tend to be less lobed, and more shallowly lobed, than those of the comparison variety 'Silver King'.
4. The new variety has a more compact habit, better basal branching, 18-24" compared to 24-36". New variety 'G18123' more compact and more densely-branched, reaching a height and width of 18-24". Comparison variety 'Silver King' is much taller and more open, about 24-36" in both height and width.
5. New variety 'G18123' flowers very late in the summer, if at all. Comparison variety 'Silver King' typically flowers by late July at 41N latitude.
6. New variety 'G18123' exhibits a high yield of cuttings which root quickly and easily. Comparison variety 'Silver King' yields fewer cuttings which tend to root more slowly than those of new variety 'G18123'.

'G18123' can also be compared to the commercially known variety *Artemisia mauiensis* 'TNARTMS' (U.S. Plant Pat. No. 30,968). These plants are similar in most horticultural characteristics. However, plants of the new cultivar 'G18123' differ in the following ways:

1. New variety 'G18123' has shallowly to not lobed leaves. Comparison variety 'TNARTMS' has finely-dissected foliage.
2. New variety 'G18123' is perennial and hardy to at least USDA zone 5. Comparison variety 'TNARTMS' is tender, and is not hardy in USDA zones colder than zone 8.
3. New variety 'G18123' is reliably perennial both in-ground and in-container. Comparison variety 'TNARTMS' is a tender annual.;

BRIEF DESCRIPTION OF THE PHOTOGRAPHS

The accompanying photograph in FIG. 1 illustrates in full color a typical plant of 'G18123' grown in a greenhouse in Bellefonte, Pa. The plant is approximately 6 months old in a 10 inch pot.

Figure 2:
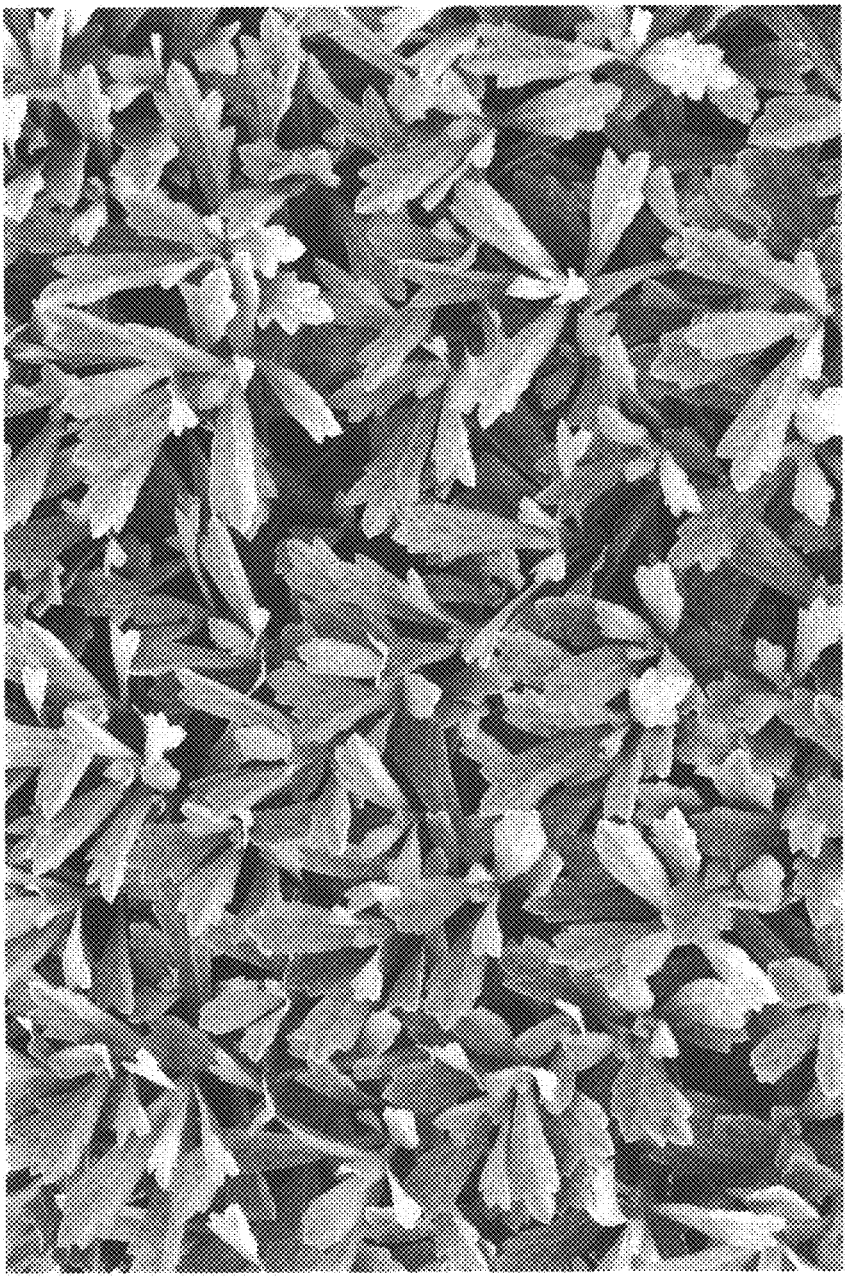

FIG. 2 illustrates a close-up view of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart 2007, except where general terms of ordinary dictionary significance are used. The following observations and measurements describe 'G18123' plants grown outdoors from Spring to early Summer in Camarillo, Calif. The growing temperature ranged from about 7° C. to 30° C. during the day and from about 5° C. to 12° C. during the night. General light conditions are bright, normal sunlight. Measurements and numerical values represent averages of typical plant types. Plants are approximately 4 months old from a rooted cutting. No chemical or photoperiodic treatments were given.

Botanical classification: *Artemisia* hybrid 'G18123'.

PROPAGATION

Root description: Fine, well-branched, fibrous, becoming slightly woody with age. Colored near Greyed-Yellow-161D and White 155A.

PLANT

Growth habit: Hardy, herbaceous perennial. Slightly flattened globular. Dense branching and foliage.
Height: Approximately 45 cm.
Plant spread: Approximately 50 cm.
Growth rate: Moderate.
Branching characteristics: Basal and lateral branching. Well branched both basally and laterally.
Length of branches: Approximately 12 to 18 cm.
Diameter branches: Approximately 5 to 6 mm.
Quantity of branches: Approximately 6 to 12 basal branches, each basal branch with 10 to 16 lateral branches.
Texture of lateral branches: Glaucous.
Color of lateral branches: Near RHS Greyed-Green 190D.
Aspect: Approximately 30° to 80° angle from center of plant.
Strength of lateral branches: Moderate, flexible.
Internode length: Average range 10 to 15 mm.
Age of plant described: Approximately 4 months old.

FOLIAGE

Arrangement: Alternate, spiraling around stem.
Average length: Average range 6 to 7.5 cm.
Average width: Average range 1.5 to 1.8 cm.
Shape of blade: Overall narrow spatulate. Typically 5 shallow lobes near apex. Lobes about 5 to 8 mm deep.
Apex: Acute.
Base: Attenuate.
Attachment: Sessile.
Margin: Entire.
Texture of top surface: Puberulent.
Texture of bottom surface: Puberulent with protruding veins.
Foliage color:

*Young foliage upper side*.—Near RHS Greyed-Green N189C covered Greyed-Green N189D.

*Young foliage under side*.—Near RHS Greyed-Green N189D.

*Mature foliage upper side*.—Near RHS Greyed-Green 191B with a strong glaucous covering near Greyed-Green N189D.

*Mature foliage under side*.—Near RHS Greyed-Green 191B with a strong glaucous covering near Greyed-Green N189D.

*Venation*.—Type: Pinnate. Venation color upper side: Near RHS Greyed-Green 192C. Venation color under side: Near RHS Greyed-Green 192D.

INFLORESCENCE

Not observed at time of description.

REPRODUCTIVE ORGANS

Not observed at time of description.

OTHER CHARACTERISTICS

Disease resistance: Neither resistance nor susceptibility to diseases or pests normal to *Artemisia* have been observed in this variety.

Drought tolerance and temperature tolerance: Hardy perennial, low temperature tolerance to USDA Zone 5, at least. Tolerates high temperatures to at least 35° C. No observed drought tolerance to date.

Fruit/seed production: Not observed to date.

What is claimed is:

1. A new and distinct cultivar of *Artemisia* plant named 'G18123' as herein illustrated and described.

* * * * *